United States Patent
Liu et al.

(10) Patent No.: US 10,736,513 B2
(45) Date of Patent: Aug. 11, 2020

(54) IMAGING DEVICES, SYSTEMS, AND METHODS OF OPERATION FOR ACOUSTIC-ENHANCED OPTICAL COHERENCE TOMOGRAPHY

(71) Applicant: CHANG GUNG UNIVERSITY, Taoyuan (TW)

(72) Inventors: Hao-Li Liu, Taoyuan (TW); Meng-Tsan Tsai, Taoyuan (TW); Chih-Kuang Yeh, Taoyuan (TW)

(73) Assignee: CHANG GUNG UNIVERSITY, Taoyuan (TW)

(*) Notice: Subject to any disclaimer, the term of this patent is extended or adjusted under 35 U.S.C. 154(b) by 458 days.

(21) Appl. No.: 15/702,574

(22) Filed: Sep. 12, 2017

(65) Prior Publication Data

US 2018/0140195 A1    May 24, 2018

(30) Foreign Application Priority Data

Nov. 18, 2016    (TW) .............................. 105137955 A

(51) Int. Cl.
| | |
|---|---|
| *A61B 5/00* | (2006.01) |
| *A61B 8/00* | (2006.01) |
| *A61B 8/08* | (2006.01) |
| *G01B 17/00* | (2006.01) |
| *G01N 21/47* | (2006.01) |
| *G01B 9/02* | (2006.01) |

(52) U.S. Cl.
 CPC .......... *A61B 5/0097* (2013.01); *A61B 5/0066* (2013.01); *A61B 8/085* (2013.01); *A61B 8/4281* (2013.01); *A61B 8/4416* (2013.01); *A61B 8/4488* (2013.01); *A61B 8/4494* (2013.01); *A61B 8/481* (2013.01); *A61B 8/5246* (2013.01); *G01B 9/02091* (2013.01); *G01B 17/00* (2013.01); *G01N 21/4795* (2013.01)

(58) Field of Classification Search
 CPC ......... A61B 5/00; A61B 8/4494; A61B 8/085; A61B 8/4281; A61B 8/4416; A61B 8/4488; A61B 8/481; A61B 8/5246; A61B 5/0066; A61B 5/0097; G01B 17/00; G01B 9/02091; G01N 21/4795
 USPC ................................ 600/454, 453, 437, 407
 See application file for complete search history.

(56) References Cited

U.S. PATENT DOCUMENTS

| | | | |
|---|---|---|---|
| 10,219,780 B2* | 3/2019 | Castella | A61B 5/0066 |
| 2002/0006248 A1* | 1/2002 | Makino | G02B 6/3522 |
| | | | 385/18 |
| 2003/0081319 A1* | 5/2003 | Hsu | G02B 5/288 |
| | | | 359/579 |
| 2003/0137669 A1* | 7/2003 | Rollins | G01B 11/2441 |
| | | | 356/479 |
| 2005/0254060 A1* | 11/2005 | Alphonse | A61B 5/0066 |
| | | | 356/479 |
| 2006/0132790 A1* | 6/2006 | Gutin | A61B 5/0066 |
| | | | 356/479 |

(Continued)

*Primary Examiner* — Oommen Jacob
(74) *Attorney, Agent, or Firm* — Cheng-Ju Chiang

(57) ABSTRACT

The present invention provides imaging devices, systems, and methods of operation for acoustic-enhanced optical coherence tomography. The systems coordinate imaging devices, optical coherence tomography (OCT), and pulsed ultrasound (FUS) and or pulsed ultrasound (PUS) to enhance the contrast of images. Moreover, the systems improve in vivo diagnosis and drug release through the utilization of sonographic enhancers such as microbubbles (MBs).

10 Claims, 15 Drawing Sheets

(56) References Cited

U.S. PATENT DOCUMENTS

| | | | |
|---|---|---|---|
| 2008/0177139 A1* | 7/2008 | Courtney | A61B 5/0035 600/109 |
| 2008/0177183 A1* | 7/2008 | Courtney | A61B 5/6852 600/463 |
| 2009/0043191 A1* | 2/2009 | Castella | A61B 5/0066 600/425 |
| 2009/0203991 A1* | 8/2009 | Papaioannou | A61B 5/0066 600/421 |
| 2012/0204648 A1* | 8/2012 | Wang | A61B 5/0095 73/606 |
| 2013/0218024 A1* | 8/2013 | Boctor | A61B 34/20 600/476 |
| 2014/0135715 A1* | 5/2014 | Lambert | A61B 18/1492 604/272 |
| 2014/0187904 A1* | 7/2014 | Razani | A61B 5/0066 600/407 |
| 2017/0164835 A1* | 6/2017 | Wiest | A61B 8/15 |
| 2017/0231598 A1* | 8/2017 | Baek | A61B 5/0004 600/454 |
| 2019/0099079 A1* | 4/2019 | Yamada | A61B 5/0035 |
| 2019/0261861 A1* | 8/2019 | Fan | A61B 5/0066 |

* cited by examiner

IMAGING DEVICES, SYSTEMS, AND METHODS OF OPERATION FOR ACOUSTIC-ENHANCED OPTICAL COHERENCE TOMOGRAPHY

1. Technical Field

Some embodiments of the present invention provide medical imaging devices, systems, and the methods of operation thereof. More particularly, the embodiments are developed with optical coherence tomography (OCT), focused ultrasound (FUS) and pulsed ultrasound (PUS).

2. Description of the Related Art

Recent development of medical imaging techniques provides a wide variety of improvement in in vivo diagnosis, real-time imaging, and non-invasive procedures.

Generally, there are three categories of medical imaging technologies based on the tomographic reconstruction algorithms. The first category reconstructs images from projection data and absorption data with the back projection algorithm. Examples of this category include X-ray computed tomography, positron emission tomography, single-photon emission computed tomography, ultrasound tomography, and optical projection tomography.

The second category reconstructs images with diffusion models. Examples of this category include electrical resistance tomography, magnetic induction tomography, diffuse optical tomography, and fluorescent molecular tomography.

Unlike the first and second categories which reconstruct images indirectly from beams passing through the objects, the source data itself obtained in the third category carries location information. Examples of this category include optical coherence tomography, confocal tomography, and ultrasound biomicroscopy.

Benefit from the nature of direct location information, the third category soon becomes the mainstream among all medical imaging technologies. And in the third category, optical coherence tomography employs a low-coherence interferometer and receives lights reflected/backscattered from specimens to generate structural images of the specimen.

The structural images can also be utilized in functional imaging to express biological properties, such as the blood velocity, birefringence, and elastic properties of tissues.

Functional imaging abilities enable to be used to observe regional functions within an organism. The change in functions usually occurs prior to the onset of structural changes. For example, the changes in blood flow, body water, $SpO_2$, or pressure may have impacts on the structure of tissues. Accordingly, functional parameters are widely used to diagnose disease at the early stage.

One of the classic examples is the angiogenesis induced by tumor. The cancer cells secrete several kinds of angiogenic growth factors to promote capillary growth. During the angiogenesis, (1) the cancer cells dissolve the peripheral connective tissue, (2) the cancer cells promote the growth of endothelial cells, (3) the endothelial cells migrate to the site of capillary growth, and (4) the endothelial cells proliferate into new vessels.

The angiogenesis plays an important role in tumor progression. Tumors require nutrients supported by blood vessels for growth and metastasis.

Therefore, angiogenesis, abnormal vessel growth, and capillary distribution may be used to identify cancer progression. Microvascular imaging, especially the OCT-based vessel imaging, is accordingly an excellent tool to diagnose tumor at the early stage and improve the survival rate.

In addition to the non-invasive diagnosis, non-invasive treatment is another branch in the field of non-invasive medicine. The technique of ultrasound drug delivery has been implemented in the areas of oncology and cardiovascular diseases. The ultrasound drug delivery is usually performed with monitoring techniques to increase the efficiency of treatments and avoid damage to normal tissues. However, these monitoring techniques are widely criticized that they fail to provide high resolution and real-time images.

Nevertheless, the combination of OCT and ultrasound drug delivery may largely improve the treatment while providing real-time data to the user. More particularly, coordinating the ultrasound techniques with OCT to enhance the imaging quality at small scale may be useful to diagnose tumor at the early stage and improve the survival rate.

SUMMARY

Some embodiments of the present invention provide novel imaging devices, systems, and methods of operation thereof. The embodiments are based on optical coherence tomography (OCT) and further combined with focused ultrasound (FUS) and/or pulsed ultrasound (PUS), as well as ultrasound sensitive medium (USM) such as microbubbles, to enhance the contrast of images. The imaging devices, systems, and methods may be used for in vivo diagnosis and drug release. Here the ultrasound sensitive medium (USM) may include lipid-based ultrasound sensitive medium/micelles, nonlipid-based ultrasound sensitive medium/micelles, or sonographic sensitive nanoparticles. The PUS defines the apparatus that emits directional ultrasound wave propagating into medium.

At least one embodiment provides an imaging device for acoustic-enhanced optical coherence tomography. The imaging device comprises an objective lens having a front lens and an optical transparent film disposed under the front lens. The imaging device also comprises a carrier containing medium, in which the carrier has a bottom made of transparent material. Moreover, in-between the optical transparent film and the bottom is space for a light path to pass through, and the piezoelectric transmitter is disposed beside the light path.

The imaging device is based on an optical coherence tomography imaging system with focused ultrasound and/or pulsed ultrasound. The imaging device is also modified to include a carrier containing a medium to reduce the energy loss of ultrasound emissions.

At least one embodiment provides a system for acoustic-enhanced optical coherence tomography. The system comprises a light source, an interferometer, a balanced detector, an analog input/output device, an amplifier, a power meter, a piezoelectric ultrasound transducer, and the imaging device disclosed in the previous embodiment. More particularly, the interferometer is in connection with the light source, the balanced detector, the analog input/output device, and the imaging device respectively. Similarly, the analog input/output device is further in connection with the balanced detector, the light source, and the amplifier respectively. The power meter is connected to the amplifier and the piezoelectric ultrasound transducer, while the imaging device is configured above the piezoelectric ultrasound transducer.

This system combines the optical coherence tomography imaging system and the focused ultrasound and/or pulsed ultrasound device, and aligns the optical beam and acoustic beam to scan and monitor the same region. The system effectively improves the efficiency of ultrasound treatments by the ability of real-time monitoring without increase in tissue damages.

At least one embodiment provides a system for acoustic-enhanced optical coherence tomography. The system comprises a light source, an interferometer, a balanced detector, an analog input/output device, an amplifier, a power meter, a piezoelectric ultrasound transducer, and the imaging device disclosed in the previous embodiment. More particularly, the interferometer is in connection with the light source, the balanced detector, and the analog input/output device respectively. Similarly, the analog input/output device is further in connection with the balanced detector and the light source. The power meter is connected to the amplifier and the piezoelectric ultrasound transducer, while the optical scanning device is configured above the piezoelectric ultrasound transducer.

This system combines the optical coherence tomography imaging system and the focused ultrasound and/or pulsed ultrasound device, and aligns the optical beam and acoustic beam to scan and monitor the same region. The system effectively improves the efficiency of ultrasound treatments by the ability of real-time monitoring without increase in tissue damages.

At least one embodiment provides a method of operating acoustic-enhanced optical coherence tomography with the system disclosed in the previous embodiment. The method comprises a step of providing a sonographic enhancer(SE) to a target, a step of applying a first ultrasound emission to the target by the piezoelectric ultrasound transducer, a step of obtaining a first acoustic signal from the target by the analog input/output device and a step of analyzing a first sequential spectral data resulting from the first acoustic signal by the analog input/output device, a step of generating a first image based on the first sequential spectral data by the analog input/output device, a step of applying a second ultrasound emission to the target by the piezoelectric ultrasound transducer, a step of obtaining a second acoustic signal from the target by the analog input/output device and a step of analyzing a second sequential spectral data resulting from the second acoustic signal by the analog input/output device, a step of generating a second image based on the second sequential spectral data by the analog input/output device, and a step of comparing the first image and the second image by the analog input/output device.

At least one embodiment provides a method of operating acoustic-enhanced optical coherence tomography with the system disclosed in the previous embodiment. The method comprises a step of providing a sonographic enhancer(SE) to a target, a step of applying a first ultrasound emission to the target by the piezoelectric ultrasound transducer, a step of obtaining a first optical signal from the target by the analog input/output device and a step of analyzing a first sequential spectral data resulting from the first optical signal by the analog input/output device, a step of generating a first B-mode image based on the first sequential spectral data by the analog input/output device, a step of applying a second ultrasound emission to the target by the piezoelectric ultrasound transducer, a step of obtaining a second optical signal from the target by the analog input/output device and a step of analyzing a second sequential spectral data resulting from the second optical signal by the analog input/output device, a step of generating a second B-mode image based on the second sequential spectral data by the analog input/output device, and a step of comparing the first B-mode image and the second B-mode image by the analog input/output device.

The method utilizes the system and the sonographic enhancer such as microbubbles to enhance the contrast of angiographic images up to 13.5 times, as compared to the conventional methods which only utilizes optical coherence tomography imaging devices. Here the ultrasound sensitive medium (e.g., sonographic enhancer) such as microbubbles may include lipid-based ultrasound sensitive medium/micelles, nonlipid-based ultrasound sensitive medium/micelles, or sonographic sensitive nanoparticles. The system also increases the depth of angiographic scanning, which is evidenced by the embodiments in the section of description of the preferred embodiments.

Some embodiments of the present invention provide imaging devices and systems for acoustic-enhanced optical coherence tomography. The embodiments reconstruct 3D images of tissues at micro scale and obtain the angiographic images thereof through non-invasive approaches. The enhanced contrast of the angiographic images is one of the benefits of the combination of optical coherence tomography imaging system, sonographic enhancer such as microbubbles, and low-energy ultrasound or low-energy pulsed ultrasound. The embodiments also can be used to scan and spot the regions of interest. Once a region of interest is selected, the energy of the focused ultrasound and/or pulsed ultrasound can then be increased to elevate the vascular permeability with the assistance from sonographic enhancer (e.g., microbubbles), and releases the drug in the vessels into the nearby tissues through the vascular walls.

Some embodiments of the present invention provide imaging devices, systems, and methods of operation for acoustic-enhanced optical coherence tomography. The embodiments can simultaneously monitor the result of ultrasound treatments. The embodiments can also be used in the field of functional imaging, such as to analyze the elastic properties of tissues, monitor moving molecules in vessels, track pharmaceutical molecules, and identify normal tissues and abnormal tissues.

DESCRIPTION OF THE PREFERRED EMBODIMENTS

Figure 1A:
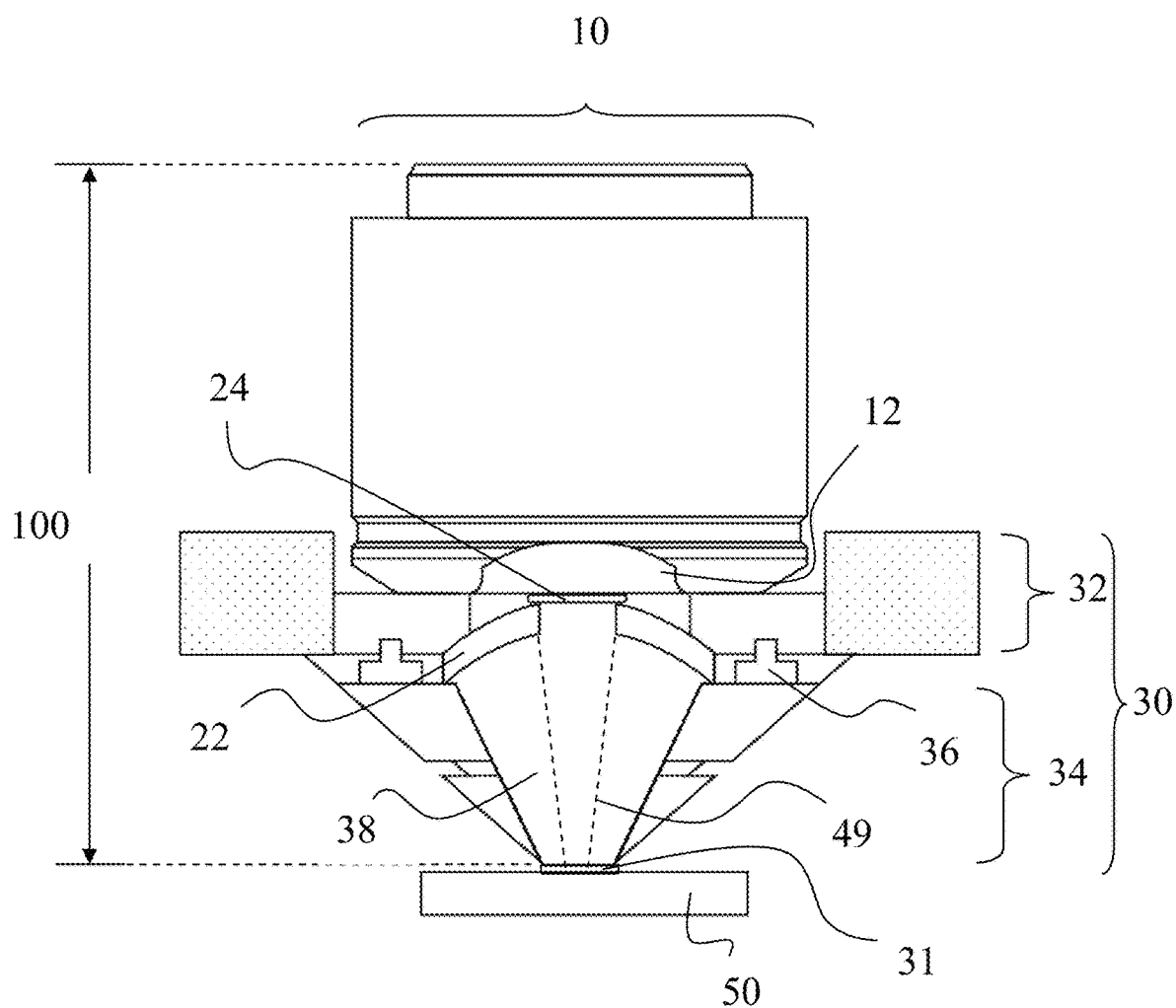
FIG. 1A illustrates a cross-sectional view of an imaging device, in accordance with some embodiments of the present invention.

Some embodiments of the present invention provide novel imaging devices, systems, and methods of operation thereof. FIG. 1A illustrates a cross-sectional view of an exemplary imaging device, in accordance with some embodiments of the present invention. The imaging device 100 comprises an objective lens 10 having a front lens 12 and an optical transparent film 24 disposed under the front lens 12. The imaging device 100 also comprises a carrier 30 containing medium 38, in which the carrier 30 is in contact with the optical transparent film 24 and has a bottom 31 made of transparent material. Moreover, in-between the optical transparent film 24 and the bottom 31 is space for a light path 49 to pass through, and the piezoelectric transmitter 22 is disposed beside the light path 49. As illustrated in FIG. 1A, the medium 38 may be in contact with the optical transparent film 24 and the piezoelectric transmitter 22.

In the embodiments, the medium 38 is a hydrophilic material and is to reduce the energy loss of ultrasound emission; the medium 38 is $H_2O$, which is transparent to ultrasound and light, in one of the preferred embodiments.

Both the optical transparent film 24 and the bottom 31 are permeable to light waves and acoustic waves.

The carrier 30 may be in unibody in some embodiments, but comprise an adapter 32 and a container 34 in some other embodiments. The adapter 32 is configured to connect the objective lens 10 and the container 34 is configured to accommodate the medium 38. Moreover, the adapter 32 and the container 34 is connected by a connector 36, which renders the container 34 detachable and allows the medium 38 to be easily replaced.

The size of the carrier 30 is at centimeter scale to match the imaging device. In a preferred embodiment, the height and width of the carrier 30 is 1.8 cm and 6.4 cm respectively.

The optical transparent film 24 may be disposed between and in contact with the carrier 30 and the piezoelectric transmitter 22.

The piezoelectric transmitter 22 is configured to received and detect the ultrasound emission, which is originated from a piezoelectric ultrasound transducer 20 (shown in FIG. 2A and FIG. 2B) and reflected by the targeted tissue. By mean of integrating the piezoelectric transmitter 22 into the imaging device 100, the scanning components in the optical coherence tomography imaging system and the focused ultrasound and/or pulsed ultrasound system are therefore minimized and merged together.

The optical transparent film 24 at the center of the piezoelectric transmitter 22 is configured for optical beams from the optical coherence tomography imaging system to pass through. With a tissue on the specimen plane 50 under the carrier 30, both the ultrasound emissions from the piezoelectric ultrasound transducer 20 and the optical beams (represented by the light path 49) from the optical coherence tomography imaging system may target the same region in the same depth of the tissue. In another embodiment is that the reflection of acoustic beams can be detected by the piezoelectric transmitter 22, while the reflection of optical beams is passing through the optical transparent film 24 to its receiver. Such synchronized activities therefore enhance the signals of the optical coherence tomographic images.

Figure 1B:
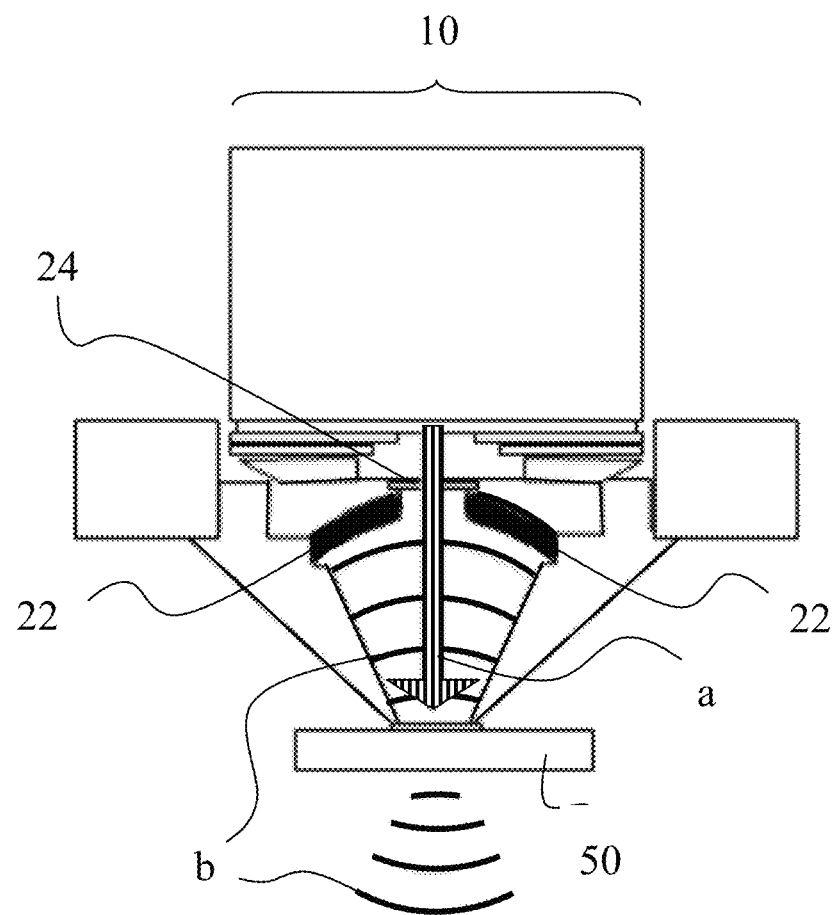
FIG. 1B is a schematic diagram illustrating the operation of an imaging device with a longitudinal-mode ultrasound transmission and a light path, in accordance with some embodiments of the present invention.
Figure 1C:
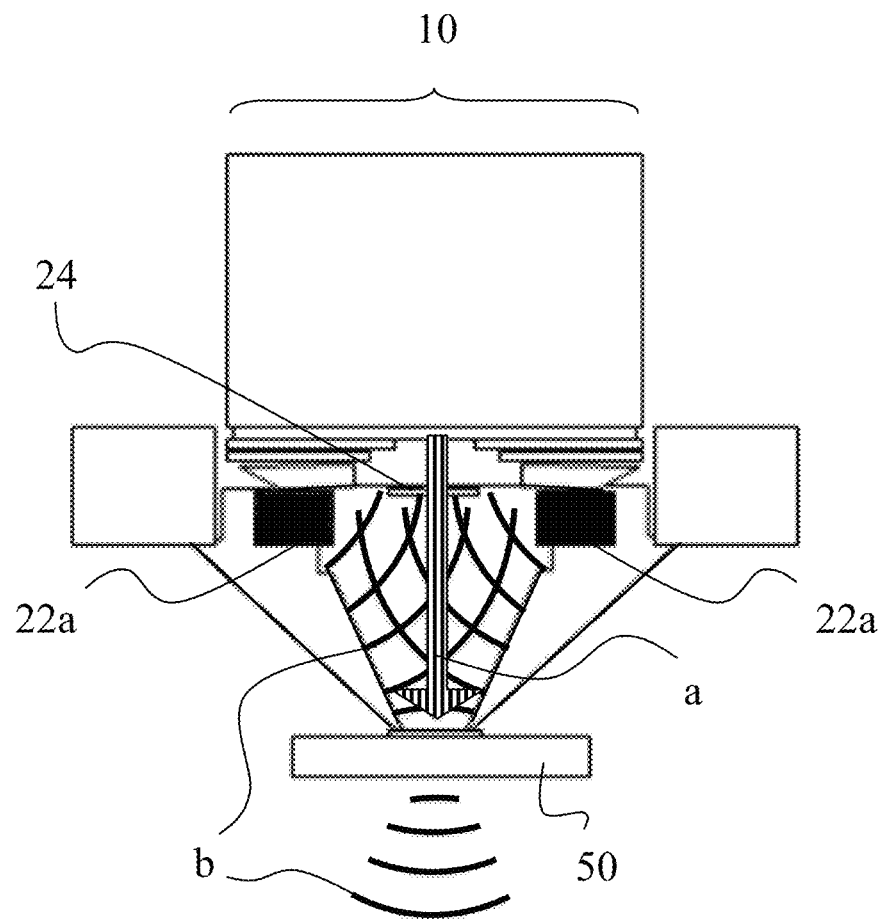
FIG. 1C is a schematic diagram illustrating the operation of an imaging device with a lateral-mode ultrasound transmission and a light path, in accordance with some embodiments of the present invention.
Figure 1D:
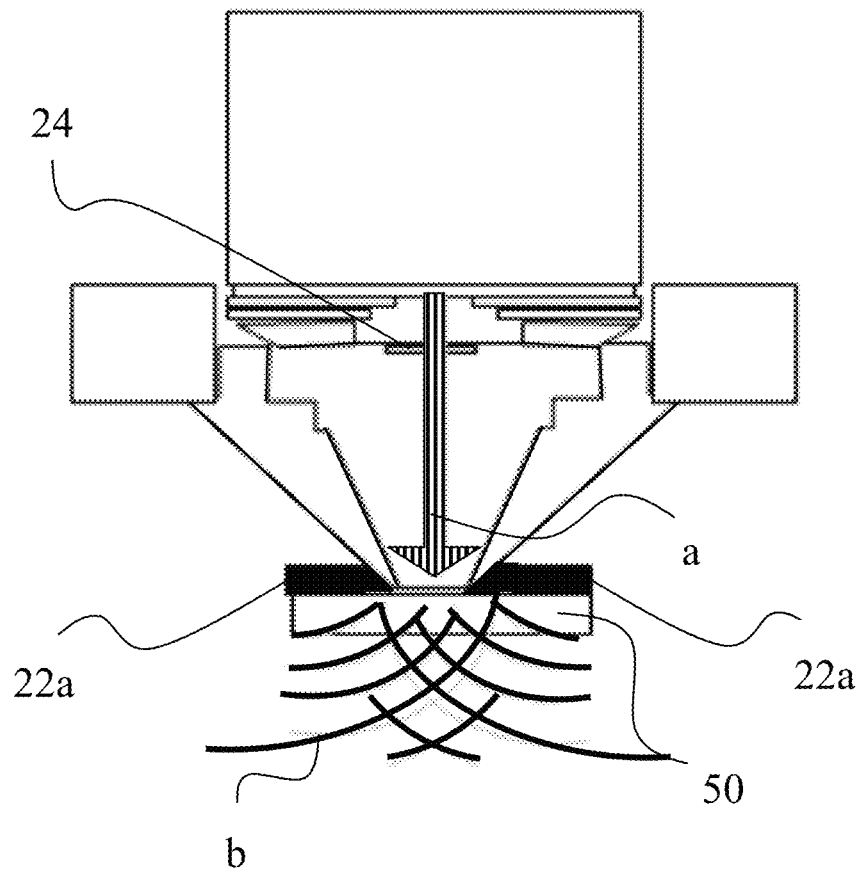
FIG. 1D is another schematic diagram illustrating the operation of an imaging device with a lateral-mode ultrasound transmission and a light path, in accordance with some embodiments of the present invention.

In some other embodiments, the acoustic beams can be combined with the light path under different integration solutions, by disposing the piezoelectric transmitter 22 at different locations. For example, the piezoelectric transmitter 22 may be disposed beside both the optical transparent film 24 and the light path 49, beside both the bottom 31 and the light path 49, or beside both the adapter 32 and the light path 49. FIG. 1B-1D provides several different embodiments of such integration solutions.

FIG. 1B is a schematic diagram illustrating the operation of an imaging device with a longitudinal-mode ultrasound transmission and a light path. To apply both the ultrasound waves and light waves to inspect a target, the embodiments employ ultrasound emissions in longitudinal mode while a hole is opened at the tip of the ultrasound probe to allow the light beams to pass through. More particularly, the hole is located at the center of the piezoelectric transmitter 22, in which the hole is on the light path 49 in FIG. 1B. In FIG. 1B, the direction of the light path 49 is represented by the arrow a and the direction of the ultrasound emission is represented by waves b. As shown in FIG. 1B, the imaging device allows ultrasound waves and light waves to scan the same target.

FIG. 1C is a schematic diagram illustrating the operation of an imaging device with a lateral-mode ultrasound transmission and a light path. To apply both the ultrasound waves and light waves to inspect a target, the embodiments employ ultrasound emissions in lateral mode while a hole is located at the center of the annular ultrasound transducer to allow the light beams to pass through. More particularly, the hole is located at the center of the circular piezoelectric transmitter 22a, in which the hole is on the light path 49 in FIG. 1C. In FIG. 1C, the direction of the light path 49 is represented by the arrow a and the direction of the ultrasound emission is represented by waves b. As shown in FIG. 1C, the ultrasound waves undergo constructive interference on the tissue to obtain the images of the tissue.

FIG. 1D is another schematic diagram illustrating the operation of an imaging device with a lateral-mode ultrasound transmission and a light path. Similarly, the embodiments employ ultrasound emissions in lateral mode while a hole is located at the center of the annular ultrasound transducer to allow the light beams to pass through. However, the annular ultrasound transducer is configured near the tissue sample. More particularly, the circular piezoelectric transmitter 22a is close to the adapter 32 of the carrier 30 and the specimen plane 50. The hole is still on the light path 49 in FIG. 1D, the direction of the light path 49 is represented by the arrow a and the direction of the ultrasound emission is represented by waves b. As shown in FIG. 1D, the ultrasound waves undergo constructive interference on a wide region of the tissue to obtain large-scale images of the tissue. These embodiments disclose several different structures to integrate the ultrasound and light. However, the present invention should not be limited to these embodiments.

Figure 2A:
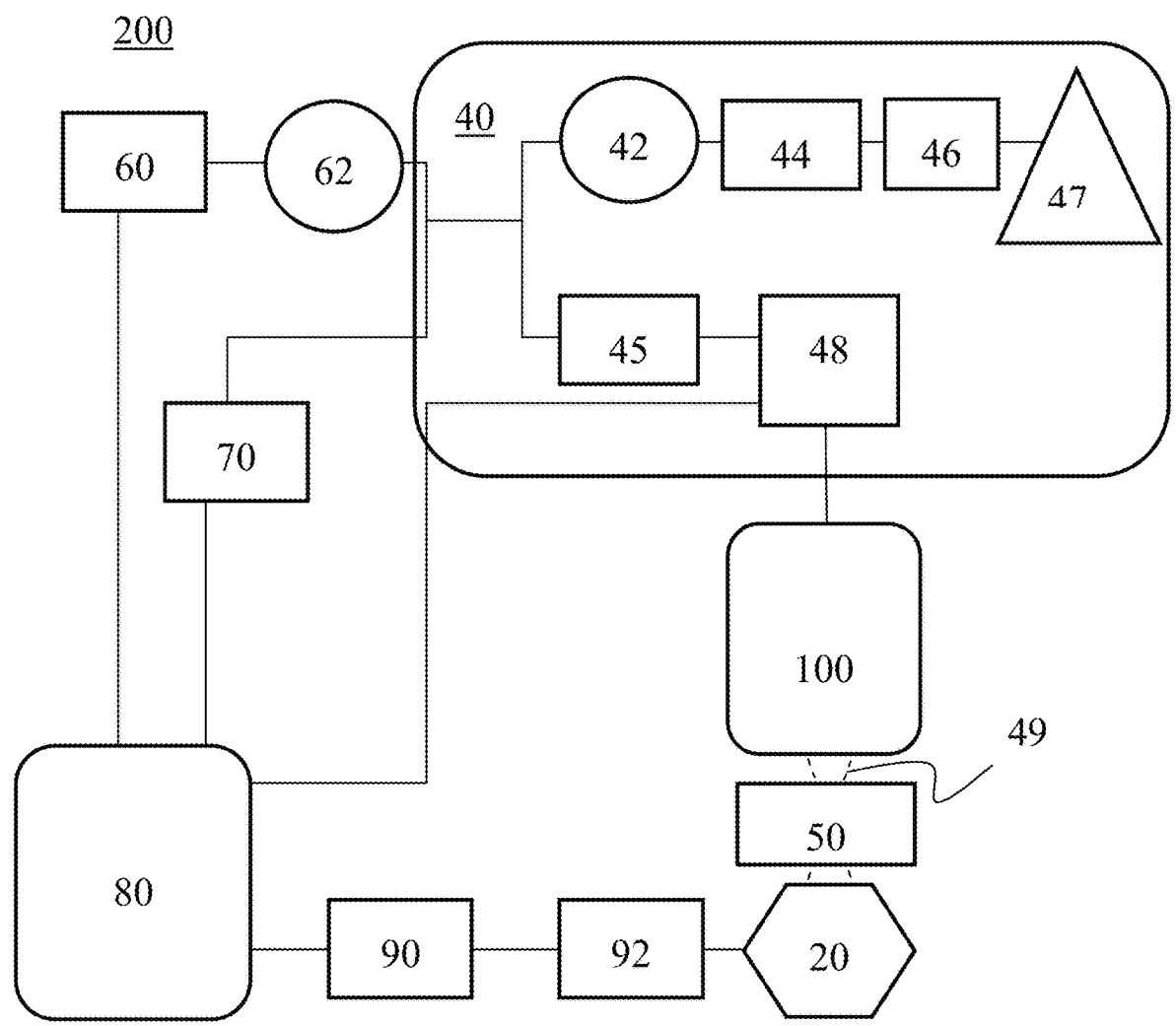
FIG. 2A and FIG. 2B illustrate a system, in accordance with some embodiments of the present invention.

FIG. 2A illustrates a system for acoustic-enhanced optical coherence tomography. The system 200 comprises a light source 60, an interferometer 40, a balanced detector 70, an analog input/output device 80, an amplifier 90, a power meter 92, an ultrasound transducer 20, and the imaging device 100 disclosed in the previous embodiments. More particularly, the interferometer 40 is in connection with the light source 60, the balanced detector 70, the analog input/output device 80, and the imaging device 100 respectively. Similarly, the analog input/output device 80 is further in connection with the balanced detector 70, the light source 60, and the amplifier 90 respectively. The power meter 92 is connected to the amplifier 90 and the ultrasound transducer 20, while the imaging device 100 is configured above the ultrasound transducer 20.

In some alternative embodiments, the system 200 comprises a light source 60, an interferometer 40, a balanced detector 70, an analog input/output device 80, an amplifier 90, a power meter 92, an ultrasound transducer 20, and the imaging device 100 disclosed in the previous embodiments. More particularly, the interferometer 40 is in connection with the light source 60, the balanced detector 70, the analog input/output device 80, and the imaging device 100 respectively. Similarly, the analog input/output device 80 is further in connection with the balanced detector 70, and the light source 60 respectively. The power meter 92 is connected to the amplifier 90 and the ultrasound transducer 20, while the imaging device 100 is configured above the ultrasound transducer 20.

Note that the light source 60 is connected to the first polarization controller 62; through the connection with the first polarization controller 62, the light source 60 is further connected with the interferometer 40.

The interferometer 40 comprises a second polarization controller 42 connected to the first polarization controller 62 which is close to the light source 60, a first collimator 44 connected to the second polarization controller 42, a second collimator 45 connected to the first polarization controller 62 which is close to the light source 60, a compensator 46 configured between the first collimator 44 and a mirror 47, and a galvanoscope 48 connected to the second collimator 45.

The balanced detector 70 is connected with the second polarization controller 42 and the second collimator 45 in the interferometer 40.

Figure 2B:
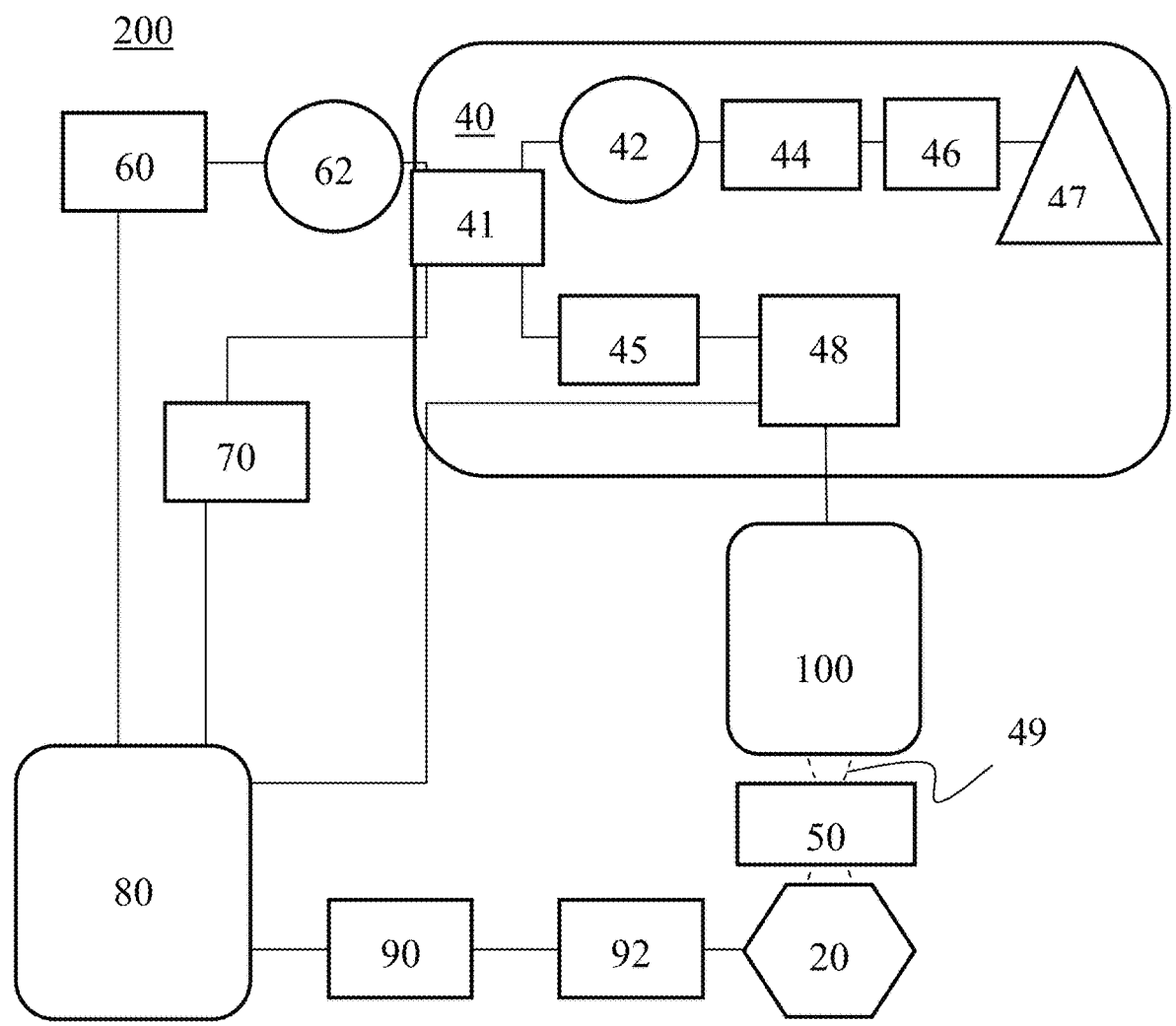

As shown in FIG. 2B, in some other embodiments, the interferometer 40 comprises a beam splitter 41 connected to the first polarization controller 62 which is close to the light source 60, a first collimator 44 connected to the second polarization controller 42, a second collimator 45 connected to a beam splitter 41 which is close to the light source 60, a compensator 46 configured between the first collimator 44 and a mirror 47, and an optical scanning device 48 connected to the second collimator 45. The balanced detector 70 is connected with the beam splitter 41.

The specimen plane 50 is configured between the imaging device 100 and the piezoelectric ultrasound transducer 20.

In some preferred embodiments, the piezoelectric ultrasound transducer 20 is a focused ultrasound and/or pulsed ultrasound device.

In some preferred embodiments, the light beam from the light source 60 is split into two light beams after passing through the first polarization controller 62; one goes to the reference arm and the other goes to the sample arm. The reference arm comprises the first collimator 44, the compensator 46, and the mirror 47, while the sample arm comprises the second collimator 45 and the galvanoscope 48. The balanced detector 70 then merges the reflected/backscattered light beams from both the reference arm and the sample arm, and removes DC signals to collect the optical signals which has been altered.

In some preferred embodiments, the light beam from the light source 60 is split into two light beams after passing through the beam splitter 41; one goes to the reference arm and the other goes to the sample arm. The reference arm comprises the first collimator 44, the compensator 46, and the mirror 47, while the sample arm comprises the second collimator 45 and the optical scanning device 48. The balanced detector 70 then merges the reflected/backscattered light beams from both the reference arm and the sample arm, and removes DC signals to collect the optical signals which has been altered.

In some preferred embodiments, the analog input/output device 80 is configured to collect and convert analog signals to digital signal, as well as output the analog signal to the amplifier 90. The analog input/output device 80 first obtains optical signals, and then analyzes such optical signals to generate sequential spectral data and images. The analog input/output device 80 may further generate a digital signal based on the result of analysis to regulate the power output of the piezoelectric ultrasound transducer 20 in a real-time manner.

The concept of this system structure is to link an optical coherence tomography imaging system based on an interferometer configuration, in which the interferometer may be a Michelson interferometer or a Mach Zehnder interferometer.

In order to align the optical beam (represented by the light path 49) from the light source 60 of the optical coherence tomography imaging system and the acoustic signal from the focused ultrasound and/or pulsed ultrasound device at the same region and depth, the piezoelectric transmitter 22 configured to detect acoustic beams is disposed on the scanning components of the optical coherence tomography imaging device (see FIG. 1). The optical beams focused by lenses is targeted on a tissue (near the specimen plane 50), and put the focus of the ultrasound emission at the depth as of the optical coherence tomography imaging system to align the optical beams and the acoustic beams. The system is therefore able to coordinate the activities of monitoring and treatments.

Figure 3:
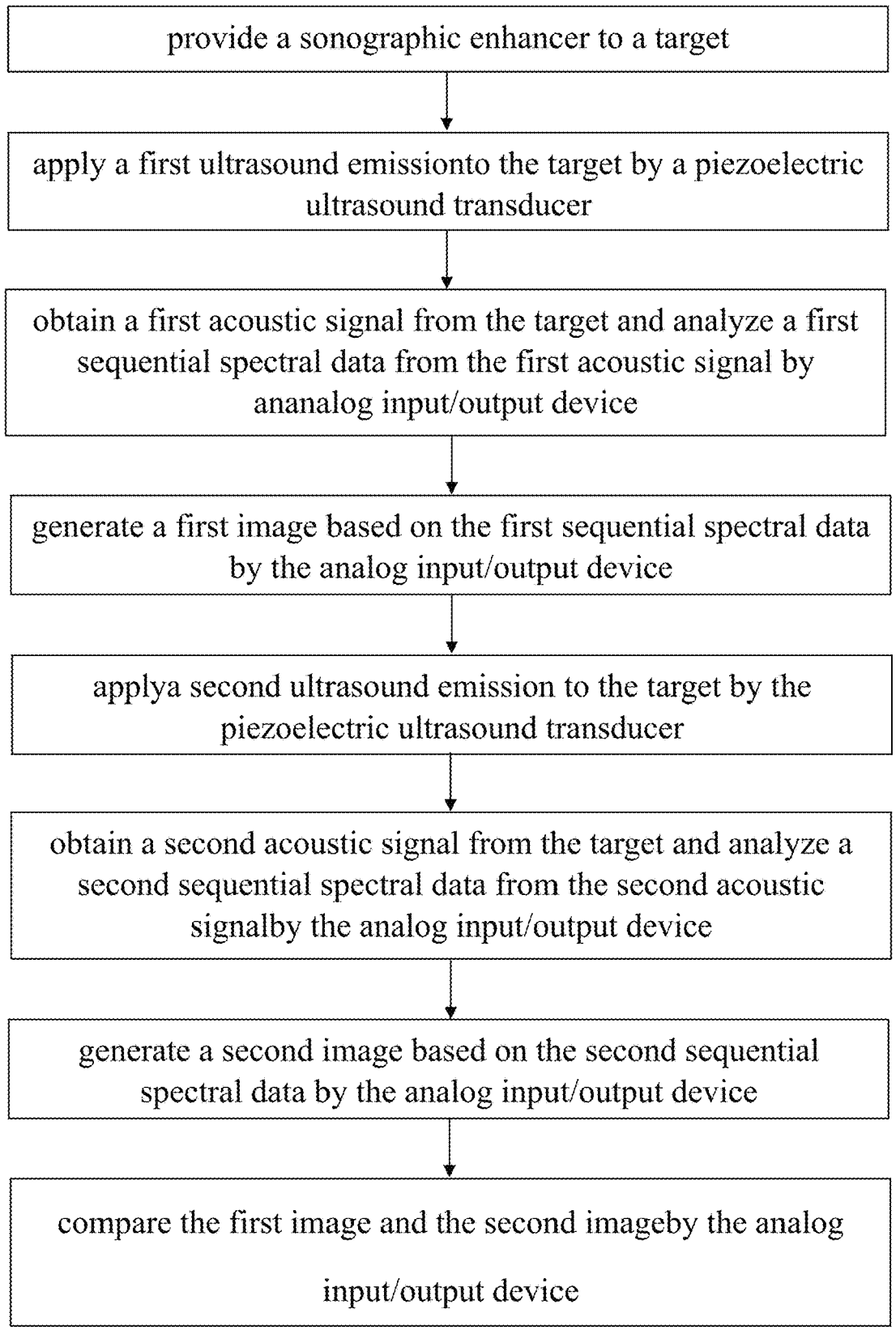
FIG. 3 illustrates a method of operation, in accordance with some embodiments of the present invention.

Some embodiments of the present invention provide methods of operating acoustic-enhanced optical coherence tomography, as illustrated in FIG. 3. The methods of operating acoustic-enhanced optical coherence tomography are based on the imaging device and system in the previous embodiments. The methods comprises a step of providing a sonographic enhancer (e.g., microbubbles) to a target, a step of applying a first ultrasound emission to the target by the piezoelectric ultrasound transducer 20, a step of obtaining a first acoustic signal from the target by the analog input/output device 80, a step of analyzing a first sequential spectral data resulting from the first acoustic signal by the analog input/output device 80, a step of generating a first image based on the first sequential spectral data by the analog input/output device 80, a step of applying a second ultrasound emission to the target by the ultrasound transducer 20, a step of obtaining a second acoustic signal from the target by the analog input/output device 80, a step of analyzing a second sequential spectral data resulting from the second acoustic signal by the analog input/output device 80, a step of generating a second image based on the second sequential spectral data by the analog input/output device 80, and a step of comparing the first image and the second image by the analog input/output device 80.

Some embodiments of the present invention provide methods of operating acoustic-enhanced optical coherence tomography, as illustrated in FIG. 3. The methods of operating acoustic-enhanced optical coherence tomography are based on the imaging device and system in the previous embodiments. The methods comprises a step of providing a sonographic enhancer (e.g., microbubbles) to a target, a step of applying a first ultrasound emission to the target by the piezoelectric ultrasound transducer 20, a step of obtaining a first optical signal from the target by the analog input/output device 80, a step of analyzing a first sequential spectral data resulting from the first acoustic signal by the analog input/output device 80, a step of generating a first B-mode image based on the first sequential spectral data by the analog input/output device 80, a step of applying a second ultrasound emission to the target by the ultrasound transducer 20, a step of obtaining a second optical signal from the target by the analog input/output device 80, a step of analyzing a second sequential spectral data resulting from the second acoustic signal by the analog input/output device 80, a step of generating a second B-mode image based on the second sequential spectral data by the analog input/output device 80, and a step of comparing the first image and the second B-mode image by the analog input/output device 80.

In some preferred embodiments, the sonographic enhancer can change light scattering condition under the presence of ultrasound energy so that the interference signals can be altered and the signal intensity of the optical coherence tomography can be changed accordingly. The ultrasound sensitive medium includes lipid-based ultrasound sensitive medium/micelles, nonlipid-based ultrasound sensitive medium/micelles, or sonographic sensitive nanoparticles, and the tissue of interest is a tumor like glioblastoma (GBM).

In some preferred embodiments, the first ultrasound emission and the second ultrasound emission are in the continuous wave mode or the pulse wave mode. In the pulse wave mode, the burst length is preferred to be between 1 ms and 100 ms; the frequency is preferred to be between 20 kHz and 100 MHz; and the acoustic pressure is preferred to be between 50 kPa and 10 MPa.

Moreover, the first sequential spectral data and the second sequential spectral data share at least one harmonic component ($2\times f_0$, $3\times f_0$, ..., etc.; where f represents fundamental emit frequency), such as an ultra-harmonic ($3/2\times f_0$, $5/2\times f_0$, ..., etc.) or sub-harmonic ones ($1/2\times f_0$).

The sonographic enhancer such as microbubbles can change light interferometric and scattering behavior under the emission of ultrasound, and can increase the signal intensity contrast of optical coherence tomographic images. To demonstrate the efficiency of the sonographic enhancer such as microbubbles, an IV tubing is placed on the specimen plane 50 (as illustrated in FIG. 2) and scanned by ultrasound emissions from the ultrasound transducer 20 at 0.9 W (equivalent to 0.3 MPa), 4.9W (equivalent to 0.66 MPa), and 9.9 W (equivalent to 0.93 MPa) respectively. Within the IV tubing, the sonographic enhancer (microbubbles) and dissolved and diluted in $H_2O$ is moving as a result of being actuated by an infusion pump. The conditions set forth here are for the purpose of demonstration only. Details can be found in FIG. 4 to FIG. 8.

Figure 4:
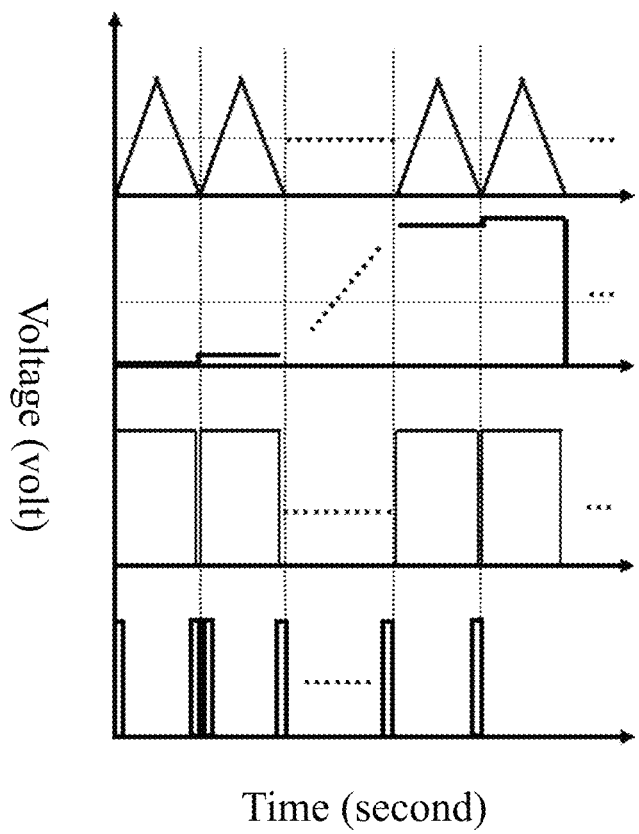
FIG. 4 is a diagram illustrates the synchronized signals of optical coherence tomography and ultrasound, in accordance with some embodiments of the present invention.

FIG. 4 is a diagram illustrates the synchronized signals of optical coherence tomography and ultrasound which may be used to provide images with superior quality of contrast. The synchronized triggering frequency between optical coherence tomography and the ultrasound emission is between 10 Hz and 100 kHz. In FIG. 4, the panels from top to bottom are the fast axis, slow axis, and frame trigger of the optical coherence tomography and the emission mode of the ultrasound respectively, which are all well-synchronized.

Figure 5:
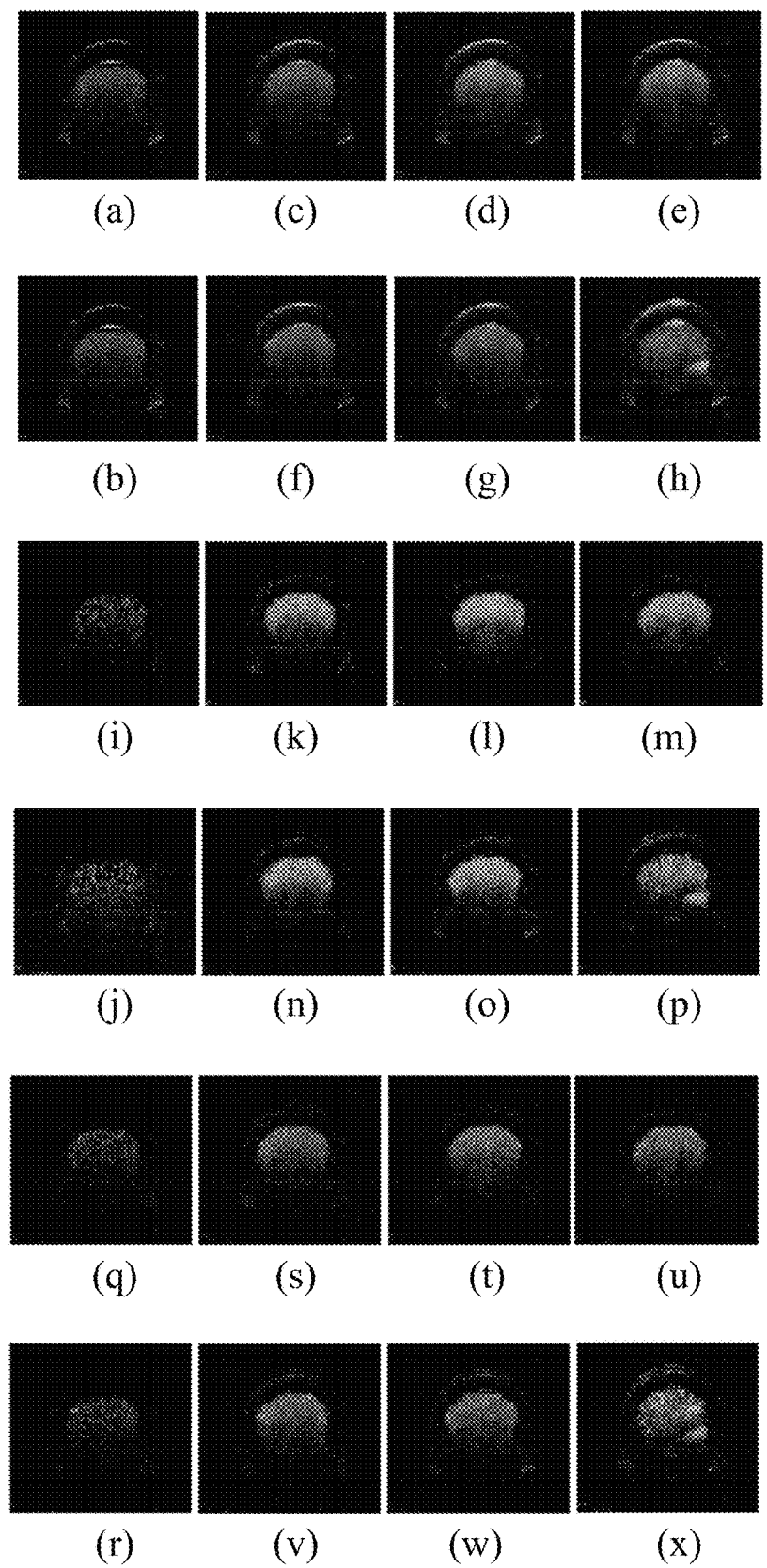
FIGS. 5(a)-5(x) of FIG. 5 are tomographic results and angiographic images under multiple conditions, in accordance with some embodiments of the present invention.

FIGS. 5(a)-5(x) of FIG. 5 are the optical coherence tomographic results and angiographic images obtained under different conditions. FIGS. 5(a)-5(h) are based on conventional optical coherence tomography (OCT) imaging device; FIGS. 5(i)-5(p) are based on a correlation-mapping optical coherence tomography (CM-OCT) imaging in combination with an imaging device disclosed in the present invention; and FIGS. 5(q)-5(x) are based on a speckle-variance optical coherence tomography (SV-OCT) imaging in combination with an imaging device disclosed in the present invention.

More particularly, FIGS. 5(a), 5(i), and 5(q) are the data without the ultrasound emissions nor the administration of ultrasound sensitive medium; FIGS. 5 (b), 5(j), and 5(r) are the data without the administration of ultrasound emissions but being applied with the ultrasound sensitive medium; FIGS. 5 (c), 5(k), and 5(s) are the data with the administration of 0.9 W ultrasound emissions in the continuous wave mode and the ultrasound sensitive medium; FIGS. 5 (f), 5(n), and 5(v) are the data with the administration of 0.9 W ultrasound emissions in the pulse wave mode with the presence of ultrasound sensitive medium; FIGS. 5 (d), 5(1), and 5(t) are the data with the administration of 4.9 W ultrasound emissions in the continuous wave mode with the presence of ultrasound sensitive medium; FIGS. 5 (g), 5(o), and 5(w) are the data with the administration of 4.9 W ultrasound emissions in the pulse wave mode with the presence of ultrasound sensitive medium; FIGS. 5 (e), 5(m), and 5(u) are the data with the administration of 9.9 W ultrasound emissions in the continuous wave mode with the presence of ultrasound sensitive medium; and FIGS. 5 (h), 5(p), and 5(x) are the data with the administration of 9.9 W ultrasound emissions in the pulse wave mode with the presence of ultrasound sensitive medium.

By comparing FIGS. 5(c)-5(h), it is observed that the signal intensity of images increases as the power of the ultrasound emissions elevates. By comparing FIGS. 5(a) and 5(b), it is observed that the signal intensity of images is increased if the ultrasound sensitive medium is present.

As evidenced by FIGS. 5 (a), 5(i), and 5(q), the signal obtained by CM-OCT and SV-OCT are slightly stronger then the signal obtained by conventional OCT even with the absence of ultrasound sensitive medium. However, as evidenced by FIGS. 5 (b), 5(j), and 5(r), the signal obtained by CM-OCT and SV-OCT are significantly stronger then the signal obtained by conventional OCT if ultrasound sensitive medium is present. Ultrasound can induce the vibration of ultrasound sensitive medium within the IV tubing and therefore enhance the dynamic scattering signal intensity detected by CM-OCT and SV-OCT.

As shown in FIGS. 5(k), 5(n), 5(s), and 5(v), even the low-power ultrasound emissions can largely boost the signal intensity detected by CM-OCT and SV-OCT. Moreover, with high-power ultrasound emissions in the pulse wave mode, the outlines of the IV tubing become clear as a result of the induction of capillary action as shown in FIGS. 5(p) and 5(x).

Figure 6A:
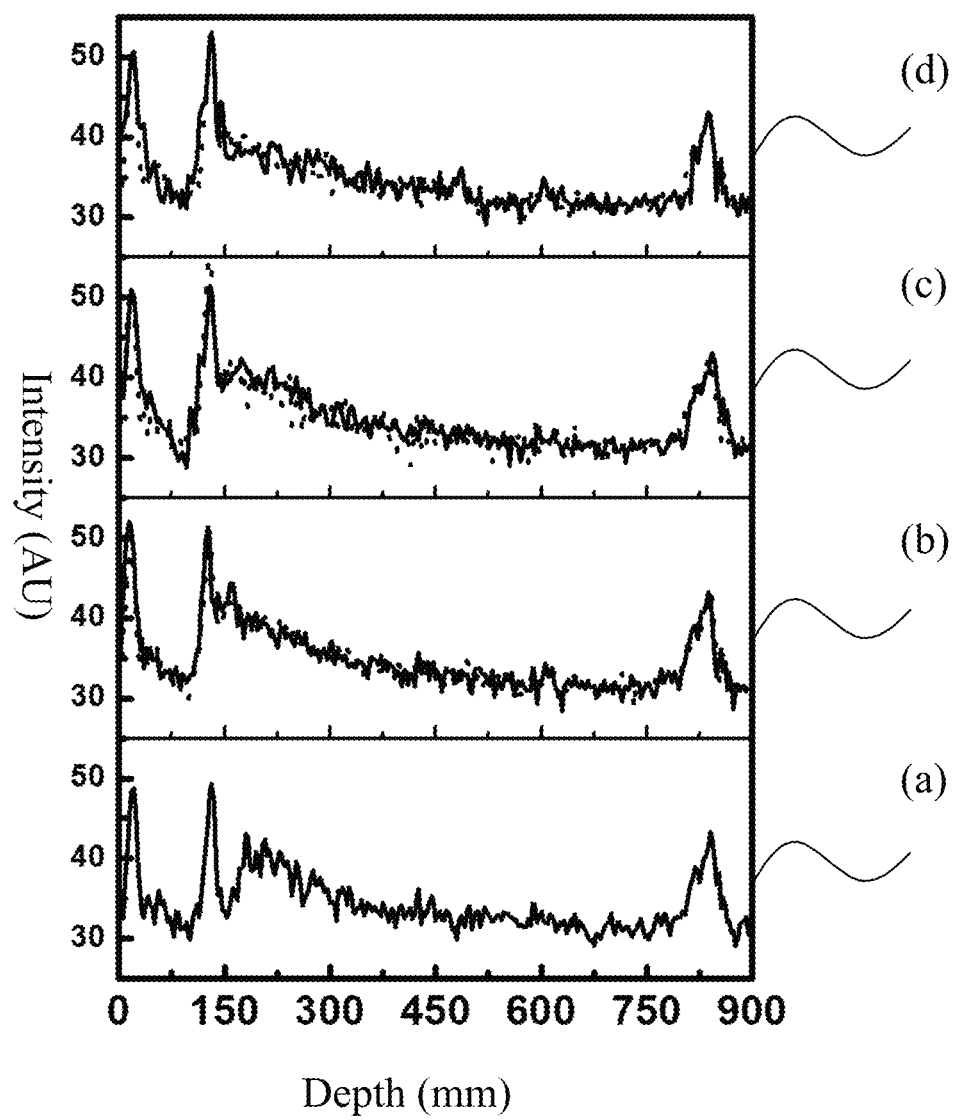
FIGS. 6A-6C are the sequential spectral data representing the signal intensities obtained by optical coherence tomography under multiple conditions, in accordance with some embodiments of the present invention.
Figure 6B:
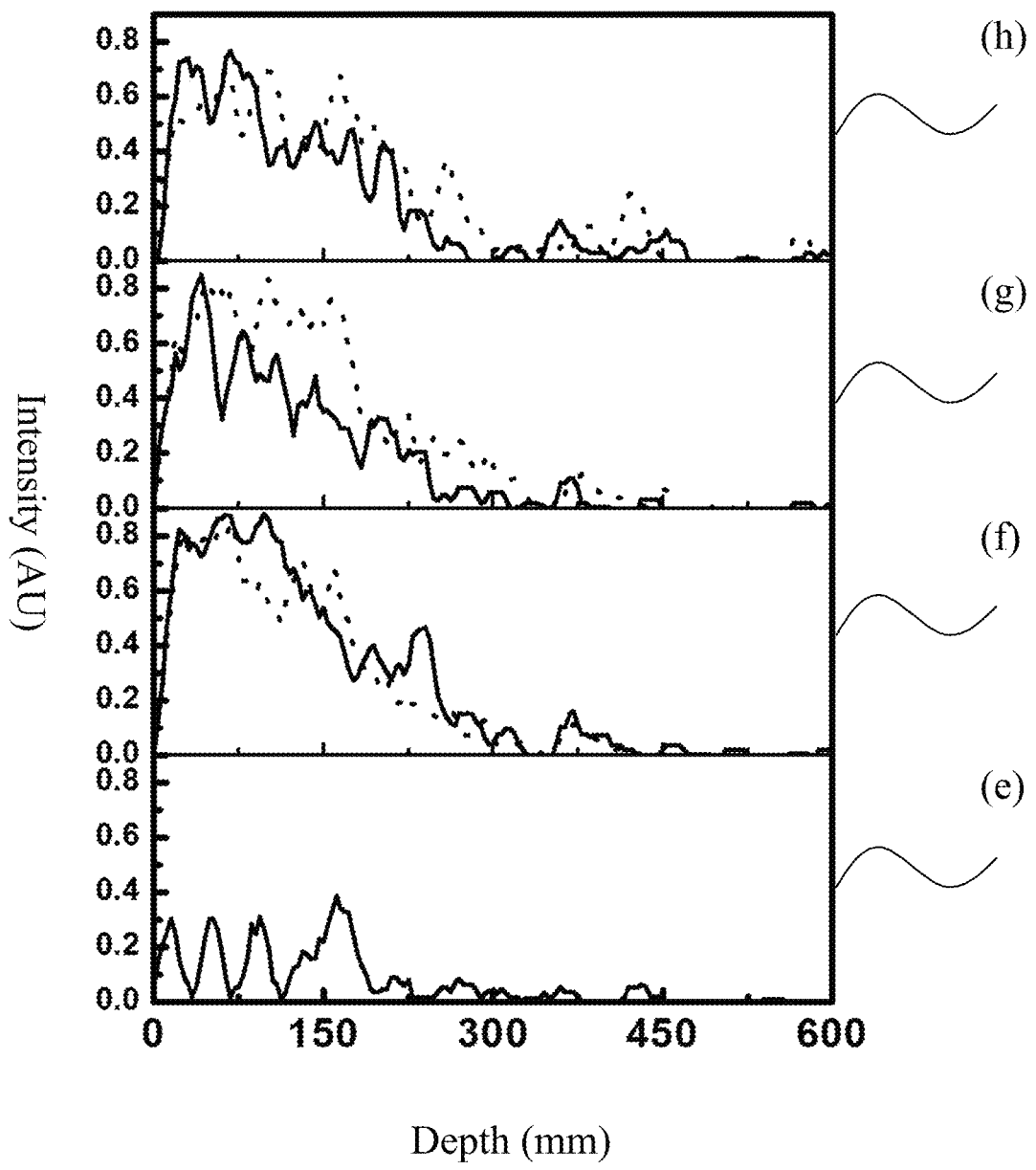
Figure 6C:
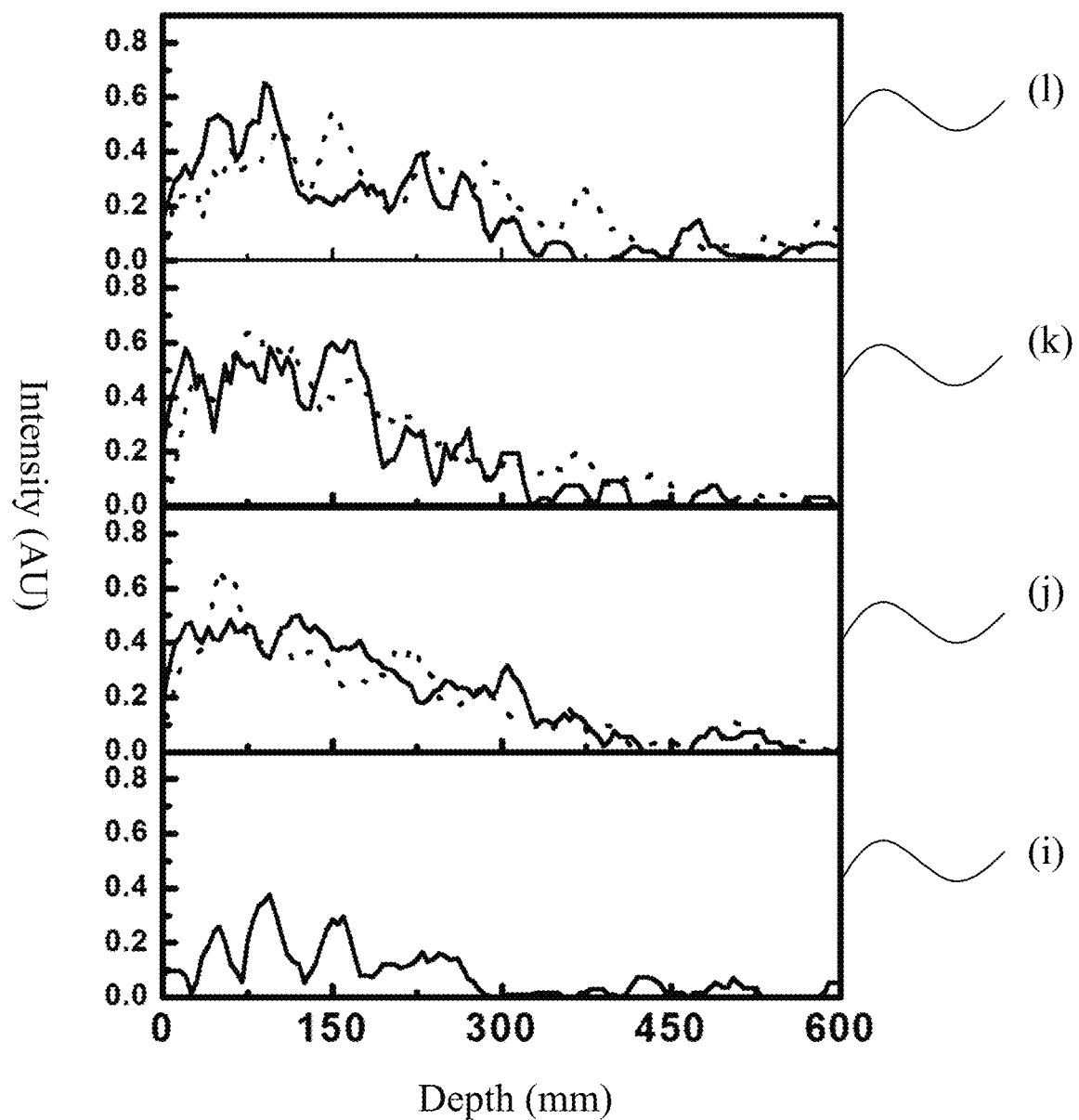

FIGS. 6A, 6B, and 6C are the sequential spectral data representing the signal intensities obtained by OCT A-scan, CM-OCT, or SV-OCT. Similarly, both CM-OCT and SV-OCT are equipped with the imaging devices disclosed in the present invention. In the figures, solid lines represent the quantitative data obtained under ultrasound emissions in the continuous wave mode and dash lines represent the quantitative data obtained under ultrasound emissions in the pulse wave mode. Panel (a) in FIG. 6A, panel (e) in FIG. 6B, and panel (i) in FIG. 6C are the data obtained without the exposure to ultrasound emissions; panel (b) in FIG. 6A, panel (f) in FIG. 6B, and panel (j) in FIG. 6C are the data obtained with the exposure to 0.9 W ultrasound emissions; panel (c) in FIG. 6A, panel (g) in FIG. 6B, and panel (k) in FIG. 6C are the data obtained with the exposure to 4.9 W ultrasound emissions; and panel (d) in FIG. 6A, panel (h) in FIG. 6B, and panel (l) in FIG. 6C are the data obtained with the exposure to 9.9 W ultrasound emissions.

Based on the data represented in arbitrary unit (AU) and obtained under multiple conditions by OCT, CM-OCT, and SV-OCT, it is obvious that even the low-power ultrasound emissions can significantly boost the signal intensity, especially under the continuous wave mode.

Figure 7A:
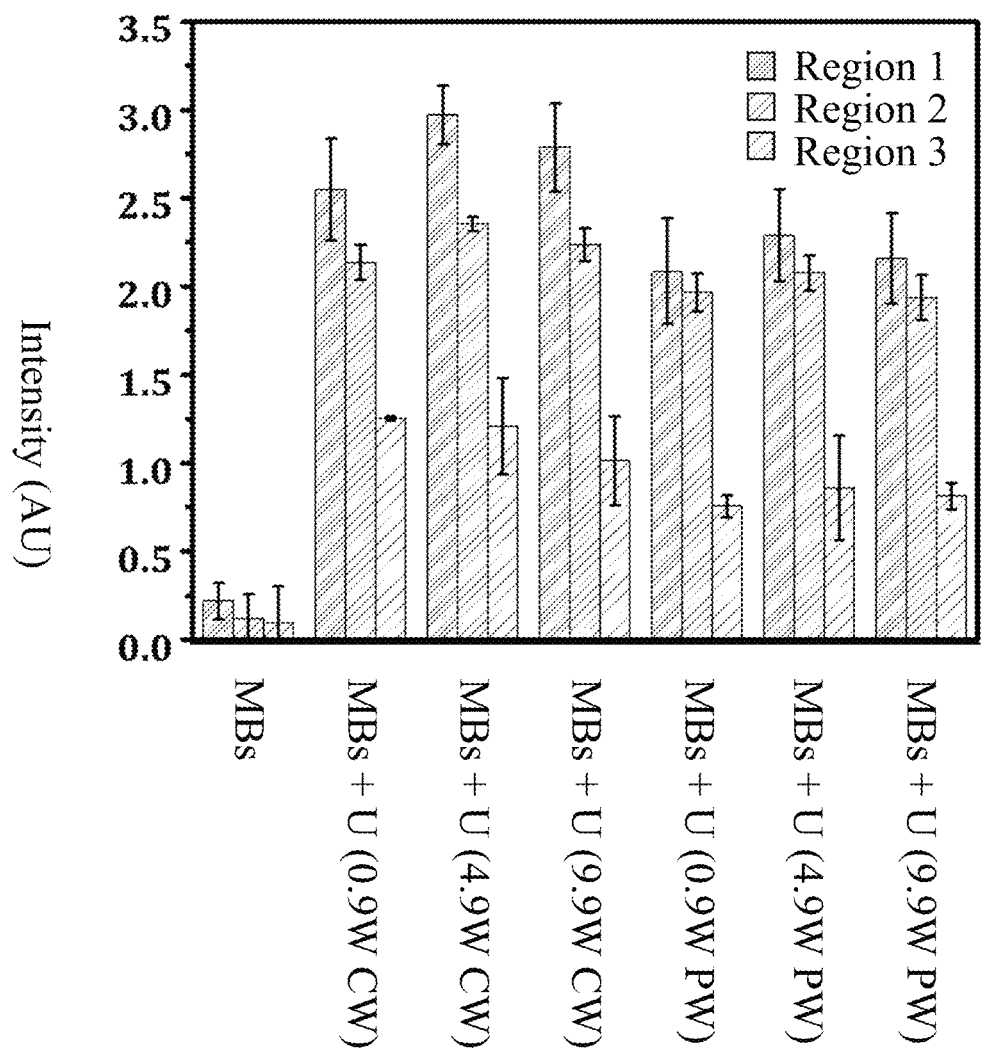
FIGS. 7A and 7B are the quantitative data representing the signal intensities obtained by optical coherence tomography under multiple conditions, in accordance with some embodiments of the present invention.
Figure 7B:
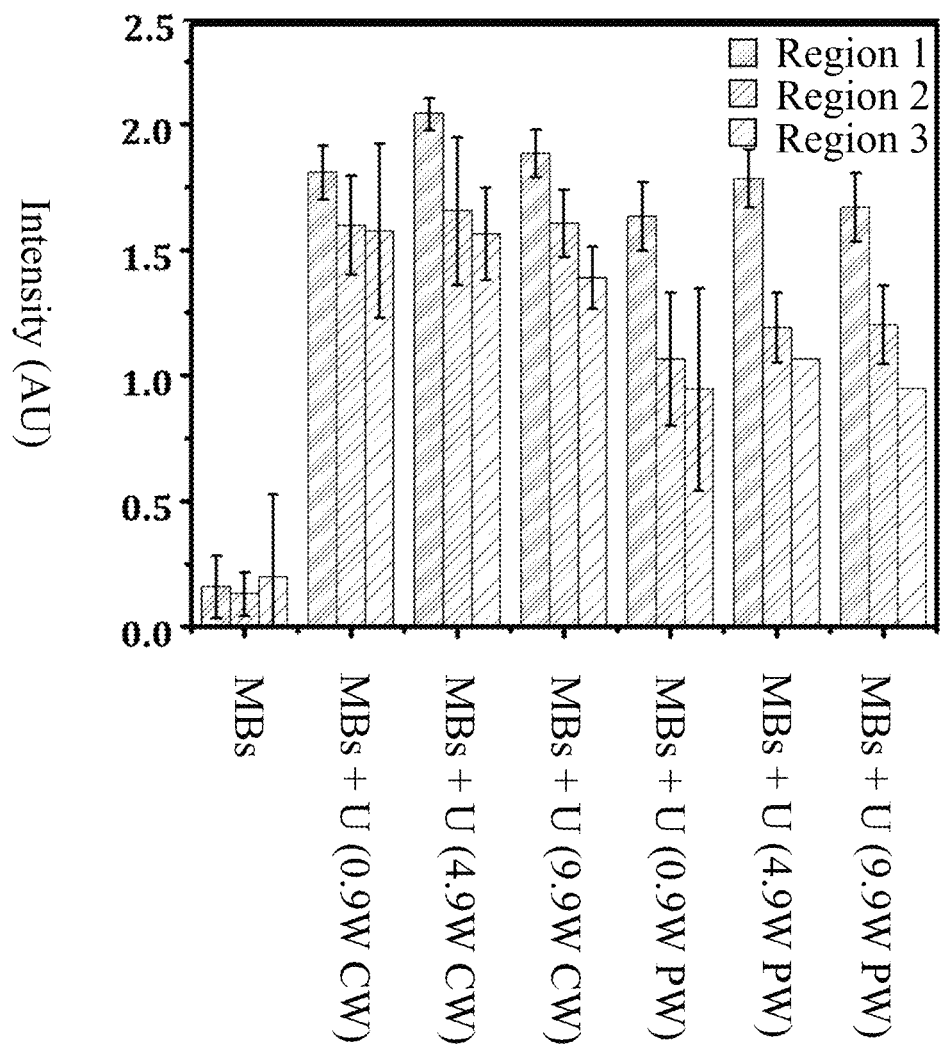

FIGS. 7A and 7B are the quantitative data representing the signal intensities of angiographic images obtained by optical coherence tomography under multiple conditions. More particularly, FIG. 7A is the data obtained by CM-OCT, and FIG. 7B is the data obtained by SV-OCT. In FIG. 7A and 7B, regions 1-3s represent the depth of scan from the surface to the inside, each with a scan area of 5,000 µm2 (i.e., 100 µm2 ×50 µm). Each region is repeatedly scanned under multiple conditions, including with ultrasound sensitive medium only, with ultrasound sensitive medium and 0.9 W ultrasound (U) in either the continuous wave mode (CW) or the pulse wave (PW) mode, with ultrasound sensitive medium and 4.9 W ultrasound in either the continuous wave mode or the pulse wave mode, and with ultrasound sensitive medium and 9.9 W ultrasound in either the continuous wave mode or the pulse wave mode. All the data are normalized to its control groups, which are the values obtained by CM-OCT or SV-OCT respectively without the ultrasound sensitive medium.

Based on the data obtained with the ultrasound sensitive medium only, the signal intensities obtained by CM-OCT fall around 0.09-0.22 AU in regions 1-3 and the signal intensities obtained by SV-OCT fall around 0.13-0.20 AU in the same regions. However, the signal intensity obtained by CM-OCT in region 1 increases to 2.08-2.97 AU after applied with both the ultrasound sensitive medium and 0.9 W, 4.9 W, or 9.9 W ultrasound emissions, which is up to 13.5 times higher than the value of with the ultrasound sensitive medium only.

Similarly, the signal intensity obtained by SV-OCT in region 1 increases to 1.63-2.04 AU after applied with both the ultrasound sensitive medium and 0.9 W, 4.9 W, or 9.9 W ultrasound emissions, which is up to 10.2 times higher than the value of with the ultrasound sensitive medium only.

In region 3, the signal intensity obtained by CM-OCT increases to 0.76-1.25 AU after applied with both the ultrasound sensitive medium and ultrasound emissions, which is up to 5.68 times higher than the value of with the ultrasound sensitive medium only; and the signal intensity obtain by SV-OCT increase to 0.94-1.57 AU after applied with both the ultrasound sensitive medium and ultrasound emissions, which is up to 7.85 times higher than the value of with the ultrasound sensitive medium only.

It is observed that the administration of ultrasound sensitive medium in combination with ultrasound emissions significantly boosts the signal intensities obtained by CM-OCT and SV-OCT, regardless of the imaging depth. The data demonstrates that the combination of medium containing ultrasound sensitive medium and ultrasound emissions can largely elevate the contrast of optical coherence tomographic images.

Figure 8:
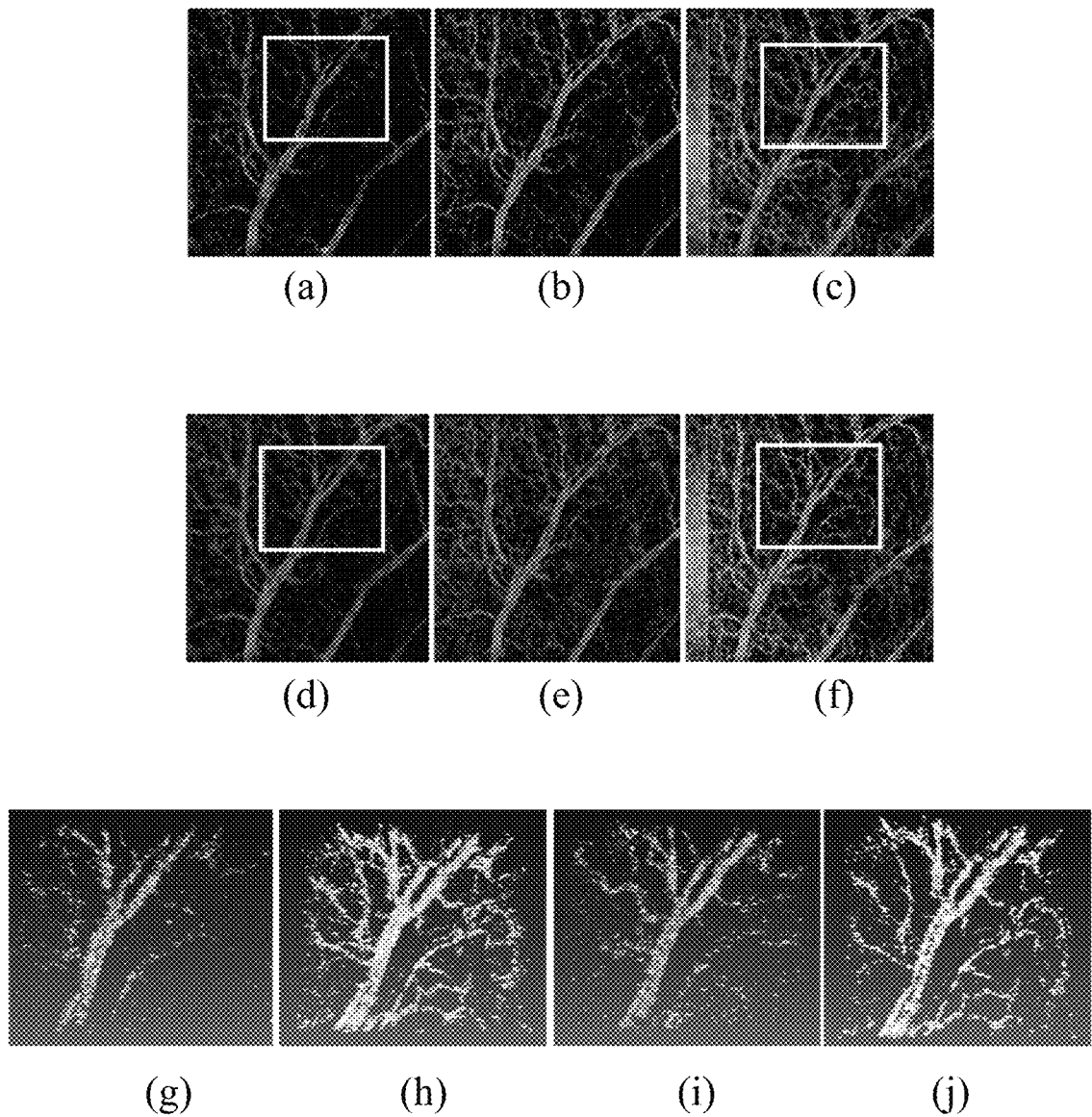
FIGS. 8(a)-8(j) of FIG. 8 are angiographic images obtained from a living animal by optical coherence tomography under multiple conditions, in accordance with some embodiments of the present invention.

FIGS. 8(a)-8(j) of FIG. 8 are angiographic images obtained from a living animal by optical coherence tomography under multiple conditions. FIGS. 8(a), 8(b), and 8(c) are based on a CM-OCT imaging system; and FIGS. 8(d), 8(e), and 8(f) are based on an SV-OCT imaging system. Both of the CM-OCT imaging system and the SV-OCT imaging system are equipped with the imaging devices disclosed in the present invention. In FIGS. 8(a) and 8(d), a medium without ultrasound sensitive medium was supplied but ultrasound emissions were not administered; in FIGS. 8(b) and 8(e), an ultrasound sensitive was supplied but ultrasound emissions were still not administered; and in FIGS. 8(c) and 8(f), an ultrasound sensitive medium and ultrasound emissions were both administered. FIGS. 8(g), 8(h), 8(i), and 8(j) are the enlarged views of the boxed regions shown in FIGS. 8(a), 8(c), 8(d), and 8(f) respectively.

More particularly, the angiographic images are of the ear of a mouse. In both the CM-OCT and SV-OCT cases, the 0.9 W ultrasound emissions in the pulse wave mode were applied to the downside of the ear and the optical coherence tomography is applied from the topside of the ear.

As evidenced by FIGS. 8(a)-8(f), the groups applied with both the ultrasound sensitive medium and ultrasound emissions have the highest contrast. The effect is applicable to both CM-OCT and SV-OCT as shown in FIGS. 8(c) and 8(f). FIGS. 8(b) and 8(e), the groups applied with the presence of ultrasound sensitive medium but without emitting ultrasound, also have enhanced contrast but not as sharp as of FIGS. 8(c) and 8(f). FIGS. 8(a) and 8(d), the groups without the administration of any ultrasound sensitive medium and ultrasound emissions, have the lowest contrast among all.

Now refer to FIGS. 8(g), 8(h), 8(i), and 8(j), the enlarged views of the boxed regions in FIGS. 8(a), 8(c), 8(d), and 8(f). The vessels are visible and clear in FIGS. 8(h) and 8(j), which prove the efficiency of the combination of ultrasound sensitive medium as well as ultrasound emissions in the improvement of the contrast of optical coherence tomographic images.

Some embodiments of the present invention provide imaging devices, systems, and methods of operation for acoustic-enhanced optical coherence tomography. The piezoelectric transmitter is included onto the scanning components of an optical coherence tomography imaging system. While the optical beams are focused on a tissue by lenses, the ultrasound emissions are also focused at the same depth and the same region of the tissue. The co-focus of the optical coherence tomography imaging system and the focused ultrasound and/or pulsed ultrasound device at the same region and depth enable the system to coordinate the activities of monitoring and treatments.

To elevate the contrast of optical coherence tomographic images, the sonographic medium such as microbubbles is supplied as a strong scattering agent for low-power ultrasound emissions in some embodiment of the present invention. This approach significantly improves the contrast of vesicular images, and provides assistance on identifying regions of interest as well. Once a region of interest is selected, the energy of the focused ultrasound and/or pulsed ultrasound can then be increased to elevate the vascular permeability and promote drug release to improve the efficiency of a treatment.

In some embodiments of the present invention, the sonographic enhancer such as microbubbles serves as a strong scattering agent in vessels to enhance the contrast of angiographic images. The same sonographic enhancer can also be used as an adjuvant of focused ultrasound and/or pulsed ultrasound treatment, such as to open the blood-brain barrier (or blood-retina-barrier) of animals and increase the permeability to allow high molecular weight compounds to enter to central nervous system. That is, the focused ultrasound and/or pulsed ultrasound can therefore temporarily remove the blood-brain barrier (or blood-retina-barrier) to allow the import of drugs into tissues in brain.

Accordingly, the imaging devices, systems, and methods of operation for acoustic-enhanced optical coherence tomography provided in the present invention have the utility in both diagnosis and treatment, especially in treating CNS or ocular diseases.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A system for acoustic-enhanced optical coherence tomography, comprising:
    a light source;
    an interferometer in connection with the light source;
    a balanced detector connected to the interferometer;
    an analog input/output device connected with the balanced detector, the interferometer, and the light source respectively;
    an amplifier connected to the analog input/output device;
    a power meter connected to the amplifier;
    an ultrasound transducer connected to the power meter; and
    an imaging device, comprising:
        an objective lens comprising a front lens;
        an optical transparent film disposed under the front lens;
        a carrier containing a medium, wherein the carrier comprises a bottom made of a transparent material; and
        a piezoelectric transmitter disposed beside a light path;
        wherein a part of the light path is between the optical transparent film and the bottom:
    wherein the imaging device is connected to the interferometer and configured above the ultrasound transducer.

2. The system as claimed in claim 1, wherein the light source is in connection with the interferometer through a first polarization controller.

3. The system as claimed in claim 2, wherein the interferometer comprises:
    a beam splitter connected to the first polarization controller
    a second polarization controller connected to the beam splitter;
    a first collimator connected to the second polarization controller;
    a second collimator connected to the beam splitter;
    a compensator connected to the first collimator;
    a mirror connected to the compensator; and
    an optical scanning device connected to the second collimator.

4. The system as claimed in claim 3, wherein the balanced detector is connected with the beam splitter.

5. The system as claimed in claim 1, wherein a specimen plane is configured between the imaging device and the ultrasound transducer.

6. A method of operating acoustic-enhanced optical coherence tomography with the system claimed in claim 1, comprising:
    providing a ultrasound sensitive medium to a target;
    applying, by the ultrasound transducer, a first ultrasound emission to the target;
    obtaining, by the analog input/output device, a first optical signal from the target and analyzing a first sequential spectral data from the first acoustic signal;
    generating, by the analog input/output device, a first image based on the first sequential spectral data;
    applying, by the ultrasound transducer, a second ultrasound emission to the target;
    obtaining, by the analog input/output device, a second optical signal from the target and analyzing a second sequential spectral data from the second acoustic signal;
    generating, by the analog input/output device, a second image based on the second sequential spectral data; and
    comparing, by the analog input/output device, the first image and the second image.

7. The method as claimed in claim 6, wherein the ultrasound sensitive medium is provided to induce light interferometric and scattering changes under the presence of the first ultrasound emission or the second ultrasound emission.

8. The method as claimed in claim 6, wherein the frequencies of the first ultrasound emission and the second ultrasound emission are between 20 kHz and 100 MHz.

9. The method as claimed in claim 6, wherein the acoustic pressures of the first ultrasound emission and the second ultrasound emission are between 50 kPa and 10 MPa.

10. The method as claimed in claim 6, wherein first sequential spectral data and the second sequential spectral data share at least one harmonic.

* * * * *